(12) United States Patent
Seixas-Mikelus

(10) Patent No.: US 11,273,140 B2
(45) Date of Patent: Mar. 15, 2022

(54) JUICE BEVERAGE FOR PREVENTION AND TREATMENT OF RENAL STONES

(71) Applicant: Stefanie A. Seixas-Mikelus, North Andover, MA (US)

(72) Inventor: Stefanie A. Seixas-Mikelus, North Andover, MA (US)

(*) Notice: Subject to any disclaimer, the term of this patent is extended or adjusted under 35 U.S.C. 154(b) by 0 days.

(21) Appl. No.: 15/335,994

(22) Filed: Oct. 27, 2016

(65) Prior Publication Data

US 2018/0028485 A1 Feb. 1, 2018

Related U.S. Application Data

(63) Continuation-in-part of application No. 14/294,125, filed on Jun. 2, 2014, now abandoned.

(60) Provisional application No. 61/952,856, filed on Mar. 13, 2014, provisional application No. 61/832,081, filed on Jun. 6, 2013.

(51) Int. Cl.
| | |
|---|---|
| *A61K 31/315* | (2006.01) |
| *A23L 2/60* | (2006.01) |
| *A23L 2/02* | (2006.01) |
| *A61K 31/194* | (2006.01) |
| *A23L 2/56* | (2006.01) |
| *A23L 2/52* | (2006.01) |
| *A23L 2/68* | (2006.01) |

(52) U.S. Cl.
CPC ............ *A61K 31/315* (2013.01); *A23L 2/02* (2013.01); *A23L 2/52* (2013.01); *A23L 2/56* (2013.01); *A23L 2/60* (2013.01); *A23L 2/68* (2013.01); *A61K 31/194* (2013.01); *A23V 2002/00* (2013.01)

(58) Field of Classification Search
CPC A23L 2/02; A23L 2/60; A61K 31/315; A61K 31/194; A23V 2002/00
See application file for complete search history.

(56) References Cited

U.S. PATENT DOCUMENTS

| | | |
|---|---|---|
| 4,774,257 A | 9/1988 | Rubin |
| 4,820,870 A | 4/1989 | Madaus et al. |
| | | (Continued) |

FOREIGN PATENT DOCUMENTS

| | | |
|---|---|---|
| CN | 1172645 A | 2/1998 |
| CN | 1284303 A | 2/2001 |
| | (Continued) | |

OTHER PUBLICATIONS

Odvina; "Comparative Value of Orange Juice versus Lemonade in Reducing Stone-Forming Risk"; 2006; Clin. J. Am. Soc. Nephrol.; 1: 1269-1274; doi: 0.2215/CJN.00800306 (Year: 2006).*

(Continued)

*Primary Examiner* — Timothy P Thomas
(74) *Attorney, Agent, or Firm* — Withers Bergman LLP; John C. Serio

(57) ABSTRACT

Described are edible citrate-rich compositions, including natural juice beverages fortified with natural occurring citrates and synthesized citrate sources that will aid in treatment and prevention of urolithiasis and other urinary tract disorders. Urolithiasis encompasses conditions in which stones are formed or reside in the urinary system and includes nephrolithiasis (stones in the kidneys), ureterolithiasis (stones in the ureter) and cystolithiasis (stones in the bladder).

3 Claims, 10 Drawing Sheets

(56) References Cited

U.S. PATENT DOCUMENTS

| | | | |
|---|---|---|---|
| 4,851,221 A | 7/1989 | Pak et al. | |
| 4,888,182 A | 12/1989 | Pak | |
| 4,966,776 A | 10/1990 | Pak | |
| 4,988,530 A | 1/1991 | Hoersten et al. | |
| 6,287,607 B2 | 9/2001 | Pak et al. | |
| 9,278,112 B2 * | 3/2016 | Goldfarb | A23L 2/52 |
| 2005/0158381 A1 | 7/2005 | Aldritt et al. | |
| 2006/0093685 A1 | 5/2006 | Mower et al. | |
| 2007/0036873 A1 | 2/2007 | Ghosal | |
| 2007/0148305 A1 * | 6/2007 | Sherwood | A23C 21/08 426/583 |
| 2009/0175843 A1 | 7/2009 | Gans | |
| 2013/0224297 A1 | 8/2013 | Roussel-Maupetit et al. | |
| 2013/0236545 A1 * | 9/2013 | Guittet | A61K 9/2054 424/468 |
| 2017/0340664 A1 | 11/2017 | Goldfarb et al. | |

FOREIGN PATENT DOCUMENTS

| | | | |
|---|---|---|---|
| CN | 105209120 A | 12/2015 | |
| IN | 247946 * | 6/2011 | |
| JP | H04-316468 A | 11/1992 | |
| WO | WO-9300020 A1 * | 1/1993 | A23L 9/10 |
| WO | 2007144778 A2 | 12/2007 | |

OTHER PUBLICATIONS

Will et al.; "Analytical composition of fruit juices from different sour cherry cultivars"; 2005; Journal of Applied Botany and Food Quality; 79: 12-16 (Year: 2005).*

Penniston et al., Quantitative assessment of citric acid in lemon juice, lime juice, and commercially-available fruit juice products. J Endourol. Mar. 2008; 22(3): 567-570.

Resnick et al. Urolithiasis A Medical and Surgical Reference. W.B. Saunders Company, 1990 p. 162.

International Search Report and Written Opinion from related PCT Application No. PCT/US2017/057858 dated Jan. 3, 2018.

Gul et al. Medical and Dietary Therapy for Kidney Stone Prevention. Korean Journal of Urology, vol. 55 No. 12. Nov. 28, 2014.

Reddy et al. Effect of Potassium Magnesium Citrate and Vitamin B-6 Prophylaxis for Recurrent and Multiple Calcium Oxalate and Phosphate Urolithiasis. Korean Journal of Urology, vol. 55, No. 6. Jun. 2014.

Hong et al. Induction of Apoptosis of Bladder Cancer Cells by Zinc-Citrate Compound. Korean Journal of Urology, vol. 53 No. 11. Jan. 1, 2012.

Examination Report in corresponding EP application No. 17866350.6 dated Apr. 6, 2021.

Office Action in corresponding corresponding CN application No. 2017800667750 dated Apr. 25, 2021.

Life Handbook for Middle-aged and Elderly People, Friends of Elderly People Magazine, Hebei Science and Technology Press, Jul. 2013.

* cited by examiner

Process Flow Diagram: Prototype Process

Process Flow Diagram: Beverage Process

Table 6 Citrate Blend Formulation

Formula Summary:
  Cranberry Lemonade:

| Ingredient | Percentage (%) |
|---|---|
| Water | 82.321% |
| Lemon Juice Concentrate | 2.744% |
| Sugar | 12.294% |
| Cranberry Juice Concentrate | 1.205% |
| Citrate Blend | |
|   Zinc Citrate | 0.020% |
|   Magnesium Citrate Anhydrous | 0.916% |
|   Monosodium Citrate | 0.500% |
| Total | 100.000% |

FIG. 3

Table 7 Citrate Blend Formulation Analysis

FIG. 4

| Sample Name: Cranberry Lemonade ||
|---|---|
| Analysis | Result |
| Elements by ICP Emission Spectrometry | |
| Calcium | 7.73 mg/Serving Size |
| Copper | 0.0695 mg/Serving Size |
| Iron | <0.125 mg/Serving Size |
| Magnesium | 371 mg/Serving Size |
| Manganese | 0.0740 mg/Serving Size |
| Phosphorus | 5.86 mg/Serving Size |
| Potassium | 76.1 mg/Serving Size |
| Sodium | 146 mg/Serving Size |
| Zinc | 19.1 mg/Serving Size |
| Specific Gravity* Density | 1.068 g/mL |
| Organic Acids* Citric Acid | 5640 mg/Serving Size |

Table 8 Citrate Blend Formulation

Berry Lemonade

| Ingredient | Percentage (%) |
|---|---|
| Water | 82.699% |
| Lemon Juice Concentrate | 2.746% |
| Sugar | 12.341% |
| Cherry Juice Concentrate | 0.418% |
| Raspberry Flavor WONF, Natural 125.17809 | 0.340% |
| Citrate Blend | |
| Zinc Citrate | 0.020% |
| Magnesium Citrate Anhydrous | 0.930% |
| Monosodium Citrate | 0.507% |
| Total | 100.000% |

FIG. 5

Table 9 Citrate Blend Formulation Analysis

FIG. 6

| Sample Name: Berry Lemonade ||
|---|---|
| Analysis | Result |
| Elements by ICP Emission Spectrometry | |
| Calcium | 6.20 mg/Serving Size |
| Copper | 0.113 mg/Serving Size |
| Iron | <0.125 mg/Serving Size |
| Magnesium | 406 mg/Serving Size |
| Manganese | 0.025 mg/Serving Size |
| Phosphorus | 5.78 mg/Serving Size |
| Potassium | 64.1 mg/Serving Size |
| Sodium | 147 mg/Serving Size |
| Zinc | 17.0 mg/Serving Size |
| Specific Gravity* Density | 1.066 g/mL |
| Organic Acids* Citric Acid | 5350 mg/Serving Size |

Table 10 Citrate Blend Formulation

Orange Strawberry

| Ingredient | Percentage (%) |
|---|---|
| Water | 80.952% |
| Orange Juice Concentrate | 11.047% |
| Sugar | 5.750% |
| Citric Acid | 0.298% |
| Citrate Blend | |
| Potassium Citrate | 0.627% |
| Magnesium Citrate Anhydrous | 0.797% |
| Monosodium Citrate | 0.418% |
| Bell Strawberry Natural Flavor WONF 133.90550 | 0.107% |
| Natural Fruit Flavor Orange 219-CB | 0.003% |
| Total | 100.000% |

FIG. 7

Table 11 Citrate Blend Formulation Analysis

FIG. 8

| Sample Name: Orange Strawberry ||
|---|---|
| Analysis | Result |
| Elements by ICP Emission Spectrometry | |
| Calcium | 18.1 mg/Serving Size |
| Copper | 0.147 mg/Serving Size |
| Iron | 0.130 mg/Serving Size |
| Magnesium | 350 mg/Serving Size |
| Manganese | 0.0337 mg/Serving Size |
| Phosphorus | 29.5 mg/Serving Size |
| Potassium | 798 mg/Serving Size |
| Sodium | 137 mg/Serving Size |
| Zinc | 0.760 mg/Serving Size |
| Specific Gravity\* Density | 1.064 g/mL |
| Organic Acids\* Citric Acid | 5510 mg/Serving Size |

Table 12 Nutritional Summary

FIG. 9

Nutritional Summary

| Product Formula Code | Targets | >4500mg | <350mg/day | | <15 mg/day | | <4500 mg/day | | <460mg/ serving | | Calories | g CHO | g Sugar |
|---|---|---|---|---|---|---|---|---|---|---|---|---|---|
| | Description | Citrate (mg/serving) | | Mg (mg/serving) | | Zn (mg/serving) | | K (mg/serving) | | Na (mg/serving) | Per serving | (g/serving) | (g/serving) |
| No citrate | Cranberry Lemonade | ---- | 2129 | ---- | 1 | ---- | 0 | ---- | 71 | ---- | 3 | 130 | 32 | 31 |
| 011614.01B | Cranberry Lemonade | 5640 | 4997 | 371 | 356 | 19 | 15 | 76 | 70 | 146 | 130 | 133 | 33 | 31 |
| No citrate | Berry Lemonade | ---- | 2080 | ---- | 11 | ---- | 0 | ---- | 68 | ---- | 3 | 130 | 33 | 30 |
| 011614.02B | Berry Lemonade | 5350 | 4990 | 406 | 361 | 17 | 15 | 64 | 67 | 147 | 132 | 130 | 33 | 30 |
| No citrate | Orange Strawberry | ---- | 2105 | ---- | 0 | ---- | 0 | ---- | 280 | ---- | 12 | 114 | 28 | 26 |
| 011614.03C | Orange Strawberry | 5510 | 4819 | 350 | 309 | 1 | 0 | 798 | 812 | 137 | 122 | 111 | 28 | 26 |

Table 13 Citrate Blend Formulation pH

FIG. 10

Summary of pH, titratable acidity, and Brix

| Product | pH | %TA | °Brix |
|---|---|---|---|
| Cranberry Lemonade | 3.50 | 1.29 | 16.80 |
| Berry Lemonade | 3.63 | 1.16 | 16.40 |
| Orange Strawberry | 4.15 | 1.42 | 15.20 |
| *pH, Titratable Acidity (%TA) and °Brix were analyzed in the QA/QC laboratory at Umass. | | | |

JUICE BEVERAGE FOR PREVENTION AND TREATMENT OF RENAL STONES

RELATED APPLICATIONS

This application claims the benefit under 35 U.S.C. § 119(e) of U.S. Application Ser. No. 61/952,856, filed Mar. 13, 2014, of U.S. Application Ser. No. 61/832,081, filed Jun. 6, 2013 and of U.S. application Ser. No. 14,294,125, filed Jun. 2, 2014. The teachings and contents of each of the referenced applications are incorporated herein by reference in their entirety.

BACKGROUND

The incidence of urolithiasis is increasing worldwide. Established risk factors for urolithiasis include dehydration, family history, obesity, bowel disease, and diets high in sodium and animal protein. Additional approaches to preventing or treating urolithiasis are needed. While compositions that are high in citrate have been utilized in the prevention of urolithiasis, the inconvenience and taste of such preparations have resulted in poor patient compliance. While there have been attempts to produce citrate rich beverages that delivers clinically significant citrate to individuals such that the occurrence of kidney stones is prevented or reduced, as shown in U.S. Pat. No. 9,278,112 ('112 patent), these compositions are believed to be tasteless beverages that are problematic resulting in poor patient compliance. Additionally, the beverage envisioned by the 112 patent requires significant volumes to achieve clinical benefit.

What is needed is a beverage that are citrate rich products—including beverages (liquids, powders, liquid concentrates) that not only prevents the onset of kidney stones but treats all forms of urolithiasis. Additionally, such a beverage to improve patient compliance should be comprised of naturally occurring sources (e.g. citrus juices) that are be fortified with naturally occurring source(s), of added citrate or in the alternative added citrates that are synthesized citrate supplements. It is also desirable to consumption of such a beverage in consumer friendly volumes results in higher urinary citrate levels and alkalization of urine such as to produce urine pH at about 6 to 7.1.

A beverage is further needed in that about 8 ounces of (one serving) is sufficient to produce desired therapeutic effect with continued use every day having a citrate level that is about 4500 mg (2000-6500 mg) per serving. A beverage having fortified citrate levels is further need that may optionally contain Ca, K, Mg, Zinc, mineral supplements, vitamin supplements and soluble fiber is also needed. It is also desirable that such a beverage will also contain lower potassium levels, lower acidity levels and lower glycemic index. Additionally, for ease of use and patient safety, it is desirable that such a beverage has a shelf life that is extended by various methods of pasteurization process.

SUMMARY

Described herein are edible, citrate-rich compositions (also referred to as edible, citrate-rich products), which include citrate-rich beverages (citrate-rich liquid compositions), powders and liquid concentrates; methods of making edible, citrate-rich compositions, including citrate-rich beverages (citrate-rich liquid compositions), powders and liquid concentrates; and methods in which such edible, citrate-rich compositions, including citrate-rich beverages (citrate-rich liquid compositions), powders and liquid concentrates are consumed (methods of therapy), which include (a) methods of preventing the onset of urolithiasis, (b) methods of reducing (partially or completely) the extent to which urolithiasis occurs and (c) methods of treating urolithiasis, by administering citrate-rich products. It is contemplated within the scope of the disclosure that the citrate-rich products or citrate-rich beverages may be a combination of naturally occurring citrate products or that naturally occurring citrate products fortified with synthesized citrate supplements. The preceding are referred to as methods of therapy/therapeutic methods.

Urolithiasis encompasses conditions in which stones are formed or reside in the urinary system and includes nephrolithiasis (stones in the kidneys), ureterolithiasis (stones in the ureter) and cystolithiasis (stones in the bladder). The most common component of urinary calculi is calcium, which is a major constituent of nearly 75% of stones. Calcium oxalate makes up about 600% of all stones; mixed calcium oxalate and hydroxyapatite, 20%; and brushite stones, 2%. Uric acid stones occur in another 10% of individuals. The citrate-rich compositions described herein are particularly useful for individuals in whom calcium and/or uric acid based stones are likely to form or have formed. It may also be used in patients who form cystine based stones.

Edible, citrate-rich compositions, such as edible, citrate-rich liquids (e.g., beverages, concentrates) and powders, can comprise naturally-occurring source(s) of citrate (such ascitrus juices), can be fortified naturally-occurring source(s) of citrate (which contain a (one or more, at least one) added citrate/citrate source and have higher citrate concentration than the corresponding product that is not fortified/includes no added citrate) or can be a combination of naturally-occurring citrate-containing source(s) and fortified citrate-rich products, such as a combination of naturally-occurring citrate-rich beverage(s) and fortified citrate-rich beverage(s).

Naturally-occurring and/or fortified citrate-rich beverages include, but are not limited to, juice, juice-water, carbonated, and non-carbonated beverages, shakes, smoothies, drinkable yogurt-type, milk products and k-cups. Citrate-rich beverages may be in a ready-to drink form or available as a concentrate, retort pouch, freeze-dried beverage, or a powder mix to be reconstituted with water or other ingestible liquid(s). Consumption of a sufficient volume of a citrate-rich composition, such as a beverage described herein, results in higher urinary citrate levels and alkalization of urine (such as to produce urine with pH of from about 6 to about 7.1, including pH of about 6.0, about 6.1, about 6.2, about 6.3, about 6.4, about 6.5, about 6.6, about 6.7, about 6.8, about 6.9, about 7.0, about 7.1) A sufficient volume is consumed to have a therapeutic effect (with continued use), which can be solubilization of developing or existing stones and/or reduction (partially or completely) of future stone development.

Typically, 8 ounces of a citrate-rich beverage (one serving) described herein is sufficient to produce the desired therapeutic effect with continued use Continued use can be over several days (e.g., two days or more, two to five days or more, a week or more, a month or more, several months, a year or more or over many weeks, months or years, including essentially every day for an individual's life. The time over which use must continue can be determined on an individual basis.

Continued use may be intermittent, in the sense that a citrate-rich composition, such as a citrate-rich beverage, may be consumed daily for a period of time (e.g., a month) and then consumption ends, consumption begins again (e.g., symptoms reoccur or life status/circumstances change) and continues for a period of time, followed by one or more additional periods during which the citrate-rich composition, such as the citrate-rich beverage is consumed daily for a period of time and consumption and one or more additional periods during which it is not consumed.

Citrate-rich beverages can be consumed by individuals (humans) known to form stones (who have previously formed stones, such as kidney stones, stones in the ureter or bladder); individuals (humans) at risk for forming kidney stones (e.g., those with a family history of kidney stone formation; men, such as men between 20 and 50 years of age); individuals (humans) in occupations predisposing to heat exposure and dehydration; individuals (humans) with bowel disease that leads to enteric hyperoxaluria; pregnant women and individuals (humans) who are non-stone formers, but who consume citrate-rich beverages described herein, such as as part of a preventative regimen (e.g., for preventing development of urolithiasis). They find use, for example, in conditions that include, but are not limited to, hypercalciuria, hyperuricosuria, hyperoxaluria, hypomagnesuria, hypocitraturia, cystinuria and gouty diathesis.

These seven conditions, appreciated on metabolic evaluation (urine collection), are known to increase risk of for development of urolithiasis. They can be used in methods of therapy for these conditions. The methods include methods of preventing the onset of at least one of the conditions, methods of reducing (partially or completely) the extent to which at least one of the condition occurs and methods of treating at least one of the conditions once it has occurred. In each case, the method is carried out by administering a citrate-rich product. Further, the edible, citrate-rich compositions can be used in military, athletic, and outer space programs in the global market. Particular advantages of the citrate-rich beverages described herein are their ease of preparation and their enjoyable taste, which will contribute to compliance by those who need or would benefit from their consumption. Liquid preparations of citrate permit longer intestinal transit time.

BRIEF DESCRIPTION OF THE FIGURES

FIG. 3 exemplifies Table 6 Citrate Blend Formulation as disclosed in the invention;

FIG. 4 exemplifies Table 7 Citrate Blend Formulation Analysis as disclosed in the invention;

FIG. 5 exemplifies Table 8 Citrate Blend Formulation as disclosed in the invention;

FIG. 6 exemplifies Table 9 Citrate Blend Formulation Analysis as disclosed in the invention;

FIG. 7 exemplifies Table 10 Citrate Blend Formulation as disclosed in the invention;

FIG. 8 exemplifies Table 11 Citrate Blend Formulation Analysis as disclosed in the invention;

FIG. 9 exemplifies Table 12 Nutritional Summary as disclosed in the invention; and FIG. 10 exemplifies Table 13 Citrate Blend Formulation pH as disclosed in the invention.

DETAILED DESCRIPTION

Figure 1:
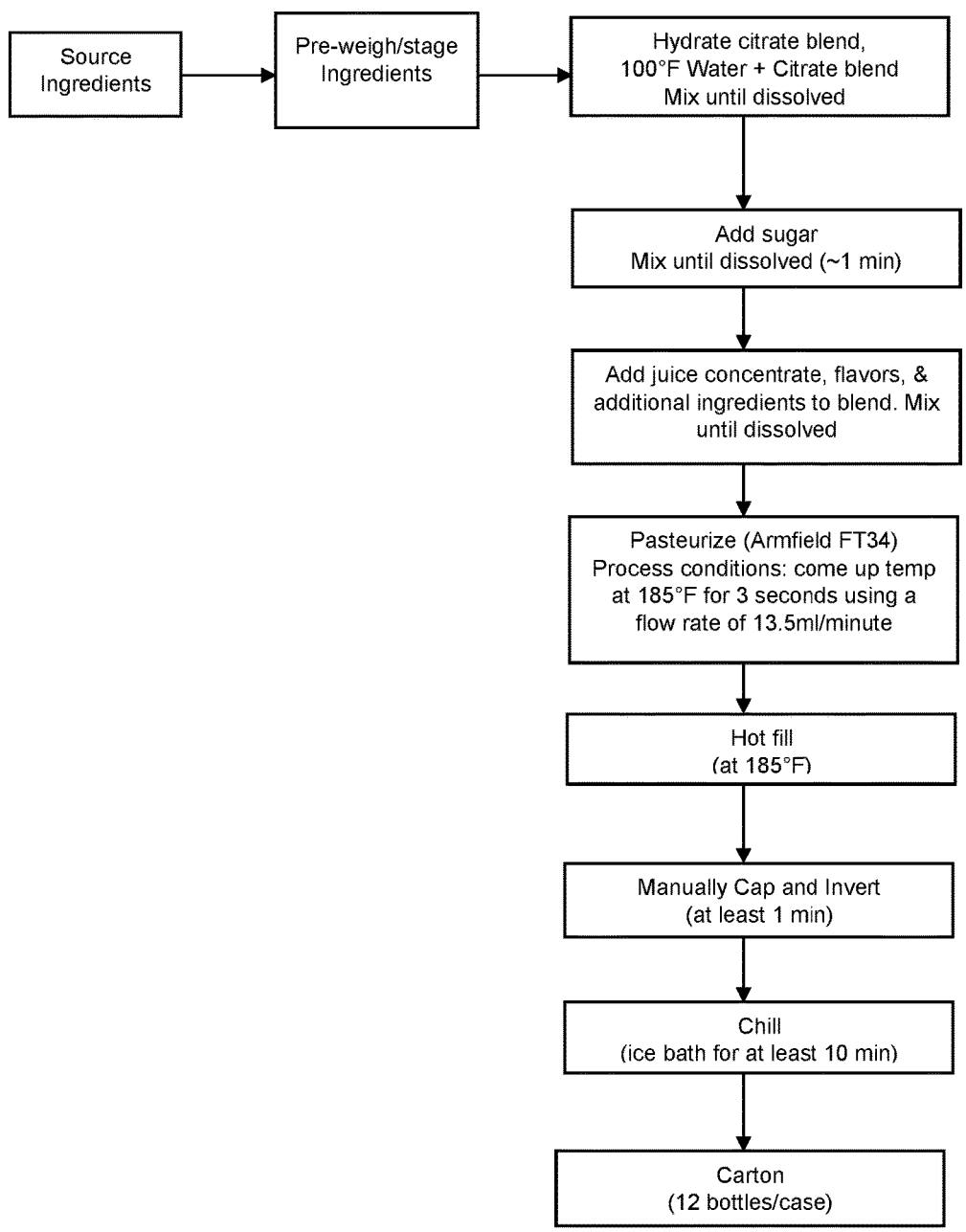
FIGS. 1 and 2 are schematic representations of methods (processes) by which citrate-rich beverages can be produced.

Edible, citrate-rich compositions, including edible, citrate-rich beverages, powders and liquid concentrates, described comprise one or more sources of citrate, such as one or more citrate-containing juice(s) and/or one or more juice concentrate(s); or one or more citrate-containing juice (s) and/or one or more juice concentrate(s) and one or more additional source(s) of citrate that is not a citrate-containing juice (referred to as a non-juice citrate source). Citrate-containing juices include, but are not limited to, orange juice, lemon juice, lemonade, tangerine juice, pineapple juice, grape juice, cranberry juice, lime juice and grapefruit juice. Concentrates of one or more of these juices can be used. Sources of citrate that are not citrate-containing juices (referred to as non-juice citrate sources) include potassium citrate, sodium citrate, calcium citrate, zinc citrate, magnesium citrate, citric acid or any combination of two, three, four, five or six of potassium citrate, sodium citrate, calcium citrate, zinc citrate, magnesium citrate, and citric acid. Non-juice citrate sources are, for example, powders (e.g., fine or crystalline powder), pills or tablets.

In particular embodiments, the citrate level of an edible citrate-rich composition, such as citrate-rich beverages, is about 4500 mg (range about 2000 mg-about 6500 mg) per serving, which equates to the typical range of oral potassium citrate given in tablets 20-60 Meq per day. It is contemplated within the scope of this disclosure that a serving would be approximately 8 ounces. On a daily (24 hour) basis, citrate intake contributed by an edible citrate-rich composition, such as a citrate-rich beverage, does not exceed about 6500 mg. The citrate level to be included in a specific citrate-rich beverage can be determined using known methods and the amount included will vary/be determined for a particular citrate-rich composition based on such considerations as the severity of the condition for which the citrate-rich beverage will be consumed, the age of the consumer and the ability to prepare a beverage acceptable to consumers.

In specific embodiments, the citrate level ranges from about 2100 mg-about 6400 mg per serving; about 2500 mg-about 6400 mg per serving; about 3000 mg-about 6400 mg per serving; about 3500 mg-about 6400 mg per serving; about 4000 mg-about 6400 mg per serving; about 4500 mg-about 6400 mg per serving; about 5000 mg-about 6400 mg per serving; or about 6000 mg-about 6400 mg per serving. In other embodiments, the citrate level is any citrate level from at least about 2100 mg per serving up to and including about 6400 mg per serving, such as at least about 2000 mg per serving; at least about 2100 mg per serving; at least about 2200 mg. per serving; at least about 2300 mg per serving; at least about 2400 mg per serving; at least about 2500 mg per serving; at least about 2600 mg per serving; at least about 2700 mg per serving; at least about 2800 mg per serving; at least about 2900 mg per serving; at least about 3000 mg per serving; at least about 3100 mg per serving; at least about 3200 mg per serving; at least 3300 mg per serving; at least 3400 mg per serving; at least 3500 mg per serving; at least about 3600 mg per serving; at least about 3700 mg per serving; at least about 3800 mg per serving; at least about 3900 mg per serving; at least about 4000 mg per serving; at least about 4100 mg per serving; at least 4200 mg per serving; at least 4300 mg per serving; at least 4400 mg per serving; at least about 4500 mg per serving; at least about 4600 mg per serving; at least about 4700 mg per serving; at least about 4800 mg per serving; at least about 4900 mg per serving; at least about 5000 mg per serving; at least about 5100 mg per serving; at least about 5200 mg per serving; at least about 5300 mg per serving; at least about 5400 mg per serving; at least about 5500 mg per serving; at least about 5600 mg per serving; at least about 5700 mg per serving; at least about 5800 mg per serving; at least about 5900 mg per serving; at least about 6000 mg per serving; at least about 6100 mg per serving; at least about 6200 mg per serving; at least about 6300 mg per serving; or at least about 6400 mg per serving.

A serving is approximately 8 fluid ounces, which can be consumed in one or more portions. For example, an 8-ounce serving can be consumed at one time or in more than one portion, such as several smaller amounts in a day, the total of which is an 8-ounce serving.

If desired, an 8 ounce serving of a citrate-rich beverage can be diluted (to produce a beverage with a lower citrate concentration).

Citrate can be provided as potassium citrate, sodium citrate, calcium citrate, zinc citrate, magnesium citrate, citric acid, other form of citrate appropriate for consumption by humans, or any combination (e.g., any combination of two, three, four, five or six of potassium citrate, sodium citrate, calcium citrate, zinc citrate, magnesium citrate, and citric acid). Sources of citrate that are not citrate-containing juices are referred to as non-juice citrate sources.

Such edible, citrate-rich compositions, such as citrate-rich beverages, may further comprise one or more (a, at least one) of the following: soluble calcium, soluble potassium, soluble magnesium, soluble zinc, mineral supplements, vitamin supplements, and soluble fiber. The edible, citrate-rich compositions may also comprise added sugar (e.g., sucrose, fructose, glucose, honey, galactose, maltose, lactose) and/or sugar alternative(s). Sugar content may be reduced (partially or completely) through the use of sugar alternatives, such as all natural sugar alternatives, such as but not limited to, honey, coconut or date sugar, *Stevia* or sugar alcohols (e.g., erythritol, xylitol, sorbitol). Such citrate-rich beverages may comprise additional ingredients including, but not limited to, any combination of juice blends of fruits and/or vegetables (e.g., for flavor), coloring, flavor, natural and artificial sweeteners, preservatives, caffeine, protein, tea and coffee. Juice blends of fruits and/or vegetables included, for example, for flavor, might not be citrate-containing, but could also include some citrate.

Edible, citrate-rich compositions, such as edible, citrate-rich beverages, can be in the form of a juice; juice-water; dairy-based product, such as milk, yoghurt; liquid concentrate, which is diluted before it is consumed or brewed or frozen, such as popsicles, or freeze-dried. Such compositions can also be in the form of a concentrate (liquid or powder, for example), which is combined with a liquid, such as milk, water, additional juice (e.g., a juice that is not a citrate-containing juice described herein, such as apple juice or pear juice), soy-based beverage, before the composition is consumed.

In some embodiments, the citrate-rich beverages are formulated to contain lower potassium levels, have reduced acidity and have lower glycemic index or any combination of the three (e.g., lower potassium levels and reduced acidity; lower potassium levels and lower glycemic index; reduced acidity and lower glycemic index; all three).

A wide variety of citrate sources can be used in making edible, citrate-rich compositions. Sources of citrate include juices that contain citrate (e.g., orange juice, lemon juice, lemonade, tangerine juice, pineapple juice, grape juice, cranberry juice, lime juice and grapefruit juice and other sources of citrate suitable/appropriate for consumption, such as citrate in tablet or powder form. The juice or juices used to produce a citrate-rich beverage can be in the form of a juice concentrate or juice in ready-to-consume form (not a juice concentrate). For example, any combination of orange juice, lemon juice, lemonade, tangerine juice, pineapple juice, grape juice, cranberry juice, lime juice, grapefruit juice, orange juice concentrate, lemon juice concentrate, lemonade concentrate, tangerine juice concentrate, pineapple juice concentrate, grape juice concentrate, cranberry juice concentrate; lime juice concentrate and grapefruit juice concentrate can be used to produce an edible, citrate-rich composition. The term juice is used here to refer to (encompasses) juice in ready-to-consume form and juice concentrate.

The citrate-rich beverages are formulated such that their consumption in sufficient quantity to prevent the onset of urolithiasis, reduce (partially or completely) the extent to which urolithiasis occurs, or treat urolithiasis results in a daily intake of not more than about 4500 mg potassium or the recommended daily intake, not more than about 1200 mg calcium or the recommended daily intake; not more than about 320-420 mg magnesium or the recommended daily intake; not more than about 40 mg of zinc or the upper tolerance level, or any combination of the foregoing. For example, citrate-rich beverages described herein typically contain, per 8 ounce serving, from about 60 mg to about 1000 mg potassium, from about 100 mg to about 410 mg magnesium, from about 1 mg to about 20 mg zinc. They may also contain per 8 ounce serving, from about 5 mg to about 500 mg calcium. In one embodiment, the volume of citrate-rich compositions, such as a citrate-rich beverage, consumed daily is from about 200 ml to about 1000 ml; in these cases, the levels of the components (e.g., citrate) are adjusted accordingly (so that consumption of the volume from about 200 ml to about 1000 ml provides the same amount of citrate as in an 8 ounce serving described herein.

The adjustment can be carried out by diluting an 8 ounce serving described herein with sufficient additional liquid that does not contain citrate to produce the desired volume. In specific embodiments, at least one 8 ounce serving is consumed each day. The volume consumed each day can be consumed in one or more doses or servings. The citrate-rich beverages can, optionally, also include (be supplemented with) sodium bicarbonate. Consumption of the citrate-rich beverage in the amounts described can result in increased urinary citrate excretion, alkalization of urine and increased urinary volume. Formulation of such beverages may be adjusted based on the consumer's health and dietary and lifestyle restrictions.

Following is a description of several embodiments of citrate-rich beverages and how they are produced. These embodiments are provided as examples only and are not to be considered limiting in any way.

Citrate-rich beverages can comprise any combination of citrate-containing edible ingredients or components available, including citrate-containing juice(s) and additional, different source(s) of citrate which are not citrate-containing juice(s) (also referred to as non-juice citrate sources).

For example, in one embodiment, a citrate-rich beverage comprises a (at least one; one or more) citrate-containing juice and an additional source of citrate that is not a citrate-containing juice (non-juice citrate source), such as one or more of the following: potassium citrate, sodium citrate, calcium citrate, zinc citrate, magnesium citrate, and citric acid. The citrate-containing juice(s) can be, for example, at least one of the following: orange juice, lemon juice, lemonade, tangerine juice, pineapple juice, grape juice, cranberry juice, lime juice and grapefruit juice. In specific embodiments, in which the citrate-rich beverage includes a (at least one; one or more) citrate-containing juice and an additional source of citrate that is not a citrate-containing juice, the citrate-rich juice is lemon juice, lime juice, orange juice, tangerine juice or grapefruit juice.

In some embodiments the citrate-rich beverage comprises at least two (two or more) citrate-containing juices and may, optionally, also include an additional source of citrate that is not a citrate-containing juice. In certain embodiments, the citrate-rich beverage includes two or more citrate-containing juices, such as any combination of two or more of orange juice, lemon juice, lemonade, tangerine juice, pineapple juice, grape juice, cranberry juice, lime juice and grapefruit juice, and does not include an additional source of citrate that is not a citrate-containing juice. In these embodiments, the two or more citrate-containing juices are any combination of two or more citrate-containing juices in amounts sufficient to produce a citrate-rich beverage that includes the desired amount of citrate, such as 4500 mg (range 2000 mg-6400 mg) per serving, which equates to the typical range of oral potassium citrate given in tablets 20-60 Meq per day. In certain embodiments a citrate rich beverage includes two or more citrate-containing juices and no additional source of citrate that is not a citrate-containing juice, the juices are any combination of two or more of lemon juice, lime juice, orange juice and grapefruit. Other citrate-containing juices can be included, such as to provide a source of citrate and to add to/alter the flavor of the citrate-rich beverage.

In embodiments in which the citrate-rich beverage includes two or more citrate-containing juices and an additional citrate source that is not a citrate-containing juice, the citrate-containing juices can be any combination of two or more of orange juice, lemon juice, lemonade, tangerine juice, pineapple juice, grape juice, cranberry juice, lime juice and grapefruit juice and the non-juice citrate source can be potassium citrate, sodium citrate, calcium citrate, zinc citrate, magnesium citrate, citric acid or any combination of two, three, four, five or six of the foregoing.

In specific embodiments, the juices are at least two of the following: lemon juice, lime juice and orange juice.

Clearly, many combinations of one or more citrate-containing juice and one or more additional source of citrate that is not a citrate-containing juice can be made, to produce inventive citrate-rich beverages, using available sources of citrate and methods, including those described herein. Such citrate-rich beverages typically provide, for example, 4500 mg citrate (range 2000 mg-6400 mg) per 8 ounce serving. Additionally, they may further comprise one or more (at least one) of the following: soluble calcium, soluble potassium, soluble magnesium, soluble zinc, mineral supplements, vitamin supplements, soluble fiber, sugar or sugar alternative. Additional ingredients that may be in such citrate-rich beverages include, but are not limited to, any combination of juice blends of fruits and/or vegetables, coloring, flavor, preservatives, caffeine, protein, tea and coffee.

Components of citrate-rich beverages described here will be selected taking into consideration such factors as the level of citrate desired, flavor, texture, appearance and other characteristics that will contribute to effectiveness, compliance and marketability of the beverages. As shown in Table 1, 2 and 5, there are many juices that can be used as sources of citrate in producing citrate-rich beverages. Additionally, Penniston and co-workers report that lemon juice contains 1.44 gm per ounce of juice; lime juice contains 1.38 gm per ounce of juice; fresh orange juice or orange juice made from concentrate contains about 0.25 gm per ounce and grapefruit juice contains 0.0068 gm per ounce. See: Penniston, K. L. et al., J. Endourol, 2008 Mar. 22 (3), 567-70. Quantitative assessment of citric acid in lemon juice, lime juice and commercially-available fruit juice products.

The citric acid content of commercially prepared juice drinks varies, depending on the manufacturer, but can range from 0.03 grams per ounce to 0.22 grams per ounce. Some artificially flavored and sweetened juices that contain no fruit can have more citric acid than the naturally-occurring citrate in citrus fruit. There are many sources of citrate other than juices (non-juice citrate source) that are commercially available; some of these are represented in Table 4.

Specific embodiments of citrate-rich beverages, which are meant to be representative of possible citrate-rich beverages encompassed by the invention, but not limiting, are presented in Table 3. In a specific embodiment, a citrate-rich beverage, such as a cranberry lemonade beverage, contains water (e.g., about 80-about 85%); juice concentrate (e.g., lemon juice concentrate; orange juice concentrate; lime juice concentrate or a combination of two or three of these) (e.g., about 2-5%); sugar (e.g., about 10-about 15%); juice concentrate (e.g., cranberry juice concentrate (e.g., about 1-about 4%); citrate (e.g., about 1-about 2.5%; e.g., zinc citrate, potassium citrate, magnesium citrate, monosodium citrate or any combination of two, three or four of these).

In a specific embodiment, a citrate-rich beverage contains water (e.g., about 80-about 83%); juice concentrate (e.g., lemon juice concentrate; orange juice concentrate; lime juice concentrate or a combination of two or three of these) (e.g., about 2-3%); sugar (e.g., about 12-about 13%); juice concentrate (e.g., cranberry juice concentrate (e.g., about 1-about 2%); citrate (e.g., total about 1.4-about 2.0%; e.g., zinc citrate, potassium citrate, magnesium citrate, monosodium citrate or any combination of two, three or four of these).

In a specific embodiment, a citrate-rich beverage contains water (e.g., about 80-about 83%); juice concentrate (e.g., lemon juice concentrate; e.g., about 2-3%, such as about any of 2.1, 2.2 2.3, 2.4, 2.5, 2.6, 2.7, 2.8, or 2.9%), sugar (e.g., about 12-about 13%); juice concentrate (e.g., cranberry juice concentrate (e.g., about 1-about 2%, such as about any one of 1.1, 1.2, 1.3, 1.4, 1.5, 1.6, 1.7, 1.8, 1.9%); citrate (e.g., total about 1.4-about 2.0%; e.g., zinc citrate, potassium citrate, magnesium citrate, monosodium citrate or any combination of two, three or four of these). In a more specific embodiment, the citrate-rich beverage contains zinc citrate (about 0.02%, to about 0.1%), magnesium citrate anhydrous (about 0.4%, to about 0.9%) and monosodium citrate (e.g., 0.1%, about 0.2%, about 0.3% about 0.4%, about 0.5%, about 0.6%, about 0.7%, about 0.8%, about 0.9%).

In a specific embodiment, a citrate-rich beverage contains water (e.g., about 80-about 83%); juice concentrate (e.g., orange juice concentrate; e.g., about 2-3%, such as about any of 2.1, 2.2 2.3, 2.4, 2.5, 2.6, 2.7, 2.8, or 2.9%); sugar (e.g., about 12-about 13%); juice concentrate (e.g., cranberry juice concentrate (e.g., about 1-about 2%, such as about any one of 1.1, 1.2, 1.3, 1.4, 1.5, 1.6, 1.7, 1.8, 1.9%); citrate (e.g., total about 1.4-about 2.0%; e.g., zinc citrate, potassium citrate, magnesium citrate, monosodium citrate or any combination of two, three or four of these).

In a specific embodiment, a citrate-rich beverage contains water (e.g., about 80-about 83%, such as about 81%, about 82%, about 83%)); juice concentrate (e.g., lemon juice concentrate; e.g., about 2-3%, such as about any of 2.1, 2.2 2.3, 2.4, 2.5, 2.6, 2.7, 2.8, or 2.9%); sugar (e.g., about 12-about 13%); juice concentrate (e.g., cranberry juice concentrate (e.g., about 1-about 2%, such as about any one of 1.1, 1.2, 1.3, 1.4, 1.5, 1.6, 1.7, 1.8, 1.9%); and citrate (e.g., total about 1.4-about 20%; e.g., zinc citrate (about 0.02%- about 0.1%), magnesium citrate (about 0.7-about 0.9%), and monosodium citrate (about 0.1-0.2%).

In a specific embodiment, such as an orange strawberry beverage, a citrate-rich beverage contains water (e.g., about 80-about 85%); juice concentrate (e.g., lemon juice concentrate; orange juice concentrate; lime juice concentrate or a combination of two or three of these)(e.g., about 5-about 13%); sugar (e.g., about 4-about 9%); citric acid (e.g., about 0.1-about 0.5%); citrate (e.g., total about 1-about 2.5%; e.g., zinc citrate, potassium citrate, magnesium citrate, monosodium citrate or any combination of two, three or four of these); flavor(s), such as natural flavor(s) (e.g., strawberry, orange, raspberry or a combination of two or three of these)(e.g., about 0.1-about 1.0° %).

In a specific embodiment, a citrate-rich beverage contains water (e.g., about 80-about 83%); juice concentrate (e.g., lemon juice concentrate; orange juice concentrate; lime juice concentrate or a combination of two or three of these) (e.g., about 10-12%); sugar (e.g., about 4-about 6%); citric acid (e.g., about 0.1-about 0.5%); citrate (e.g., total about 1-about 2.5%; e.g., zinc citrate, potassium citrate, magnesium citrate, or any combination of two or three of these); flavor(s), such as natural flavor(s) (e.g., strawberry, orange, raspberry or a combination of two or three of these) (e.g., about 0.001-about 1.0%). In a further embodiment, a citrate-rich beverage contains water (e.g., about 80%, about 81%, about 82% or about 83%); juice concentrate (e.g., orange juice concentrate or lime juice) (e.g., about 10-12%); sugar (e.g., about 4-about 6%); citric acid (e.g., about 0.1, about 0.2%, about 0.3%, about 0.4%); citrate (e.g., total about 1-about 2.0%; e.g., zinc citrate (about 0.1%, about 0.2%; about 0.3%; about 0.4%), potassium citrate (about 0.2%, about 0.3%, about 0.4%; about 0.5%; about 0.6%), magnesium citrate (e.g., about 0.4%, about 0.5%, about 0.6%, about 0.7%), or any combination of two or three of these); fruit flavor(s), such as natural flavor(s)(e.g., strawberry, orange, raspberry or a combination of two or three of these) (e.g., about 0.001-about 1.0%).

In a specific embodiment, a citrate-rich beverage, such as a berry lemonade beverage, contains water (e.g., about 80-about 85%); juice concentrate (e.g., lemon juice concentrate; orange juice concentrate; lime juice concentrate or a combination of two or three of these)(e.g., about 2-5%); sugar (e.g., about 10-about 15%); juice concentrate (e.g., cherry juice concentrate, cranberry juice concentrate (e.g., about 0.2-about 4%); citrate (e.g., about 1-about 2.5%; e.g., zinc citrate, potassium citrate, magnesium citrate, monosodium citrate or any combination of two, three or four of these); and fruit flavor, such as natural flavor (e.g., raspberry, orange, strawberry or a combination of two or three of these) (e.g., about 0.1% to about 0.6%). Ina specific embodiment, a citrate-rich beverage contains water (e.g., about 80, about 81%, about 82%, about 83%, about 84%; about 85%); juice concentrate (e.g., lemon juice concentrate; e.g., about 2%, about 3%, about 4%), sugar (e.g., about 10%, about 11%, about 12%, about 13%, about 14%, about 15%); juice concentrate (e.g., cherry juice concentrate; e.g., about 0.2%, about 0.3%, about 0.4%, about 0.5%); citrate (e.g., total about 1%-about 2.5%; e.g., zinc citrate (e.g. about 0.02%, about 0.03%, about 0.4%, about 0.5%), magnesium citrate (e.g., 0.6%, about 0.7%, about 0.8%, about 0.9%, about 1.0%), monosodium citrate (e.g., about 0.05%, about 0.06% about 0.07%, about 0.08%, about 0.09%, about 0.10%, about 0.11%, about 0.12%); and fruit flavor, such as natural flavor (e.g., raspberry flavor; e.g., about 0.1%, about 0.4%, about 0.5%, about 0.6%).

A specific embodiment is an edible citrate-rich composition in which citrate is present at (the composition comprises) a level of from about 2000 mg citrate to about 6400 mg citrate per 8 ounce serving.

In a further embodiment of the edible citrate-rich composition, citrate is present at about 4500 mg per 8 ounce serving and the source of citrate is at least one source selected from the group consisting of a citrate-containing juice, potassium citrate, sodium citrate, magnesium citrate, zinc citrate citric acid, and calcium citrate. The composition, in one embodiment of the edible citrate-rich composition, is a beverage and, for example, the citrate-containing juice is at least one of the following: orange juice, lemon juice, lemonade, tangerine juice, lime juice, pineapple juice, grape juice, cranberry juice and grapefruit juice.

Any of these citrate-rich compositions can further comprise one or more of the following: soluble calcium, soluble potassium, soluble magnesium, mineral supplements, vitamin supplements, soluble fiber in sugar-containing preparation and soluble fiber in sugar-free preparation. Any of these citrate-rich compositions can comprise/is constituted with at least one (a, one or more) of water, juice, milk, and yogurt and, in some embodiments, the composition is a liquid, frozen, or freeze-dried. The citrate-rich composition can further comprise sodium bicarbonate.

A further embodiment is a method of reducing (partially or completely) the extent to which urolithiasis occurs in an individual or of treating urolithiasis in an individual, comprising administering a therapeutically effective amount of a citrate-rich composition of any one of the embodiments described herein to the individual, wherein the therapeutically effective amount of the citrate-rich composition is administered in at least one dose and can be administered in multiple doses over time. In some embodiments, the therapeutically effective amount of the citrate-rich composition is administered in multiple daily doses or portions (multiple daily doses or portions per 24 hour period).

A further embodiment is a method of increasing urinary citrate levels and producing alkalization of urine in an individual in need thereof, comprising administering a citrate-rich composition of any one of the embodiments described herein to the individual in an amount sufficient to increase citrate levels in the individual's urine and produce urine of pH from about 6 to about 7.1, wherein the citrate-rich composition is administered in at least one dose per day (at least one dose per 24 hour period) and can be administered in multiple doses overtime. In a specific embodiment, the citrate-rich composition is administered in one daily dose (one dose in a 24-hour period). In a different embodiment, the citrate-rich composition is administered in more than one daily dose (more than one dose in a 24-hour period). In alternative embodiments, the citrate-rich composition is administered for more than one day and can be administered over an extended period of time, which can be two or more days, a week or more, a month or more, many months, a year or more, many years or as needed throughout the individual's life.

One embodiment is a method of reducing (partially or completely) the extent to which urolithiasis occurs in an individual or of treating urolithiasis in an individual, comprising administering a citrate-rich composition that comprises from about 2000 mg citrate to about 6400 mg citrate per 8 ounce serving to the individual, wherein the 8 ounce serving of the citrate-rich composition is administered in at least one dose or portion per day (24 hour period) and can be administered in multiple doses overtime.

Methods by which the beverages can be produced are described below. They are representative of methods that can be used and are not intended to be limiting in any way. All embodiments of the citrate-rich beverages encompassed by the invention can be made by the methods described herein.

Figure 2:
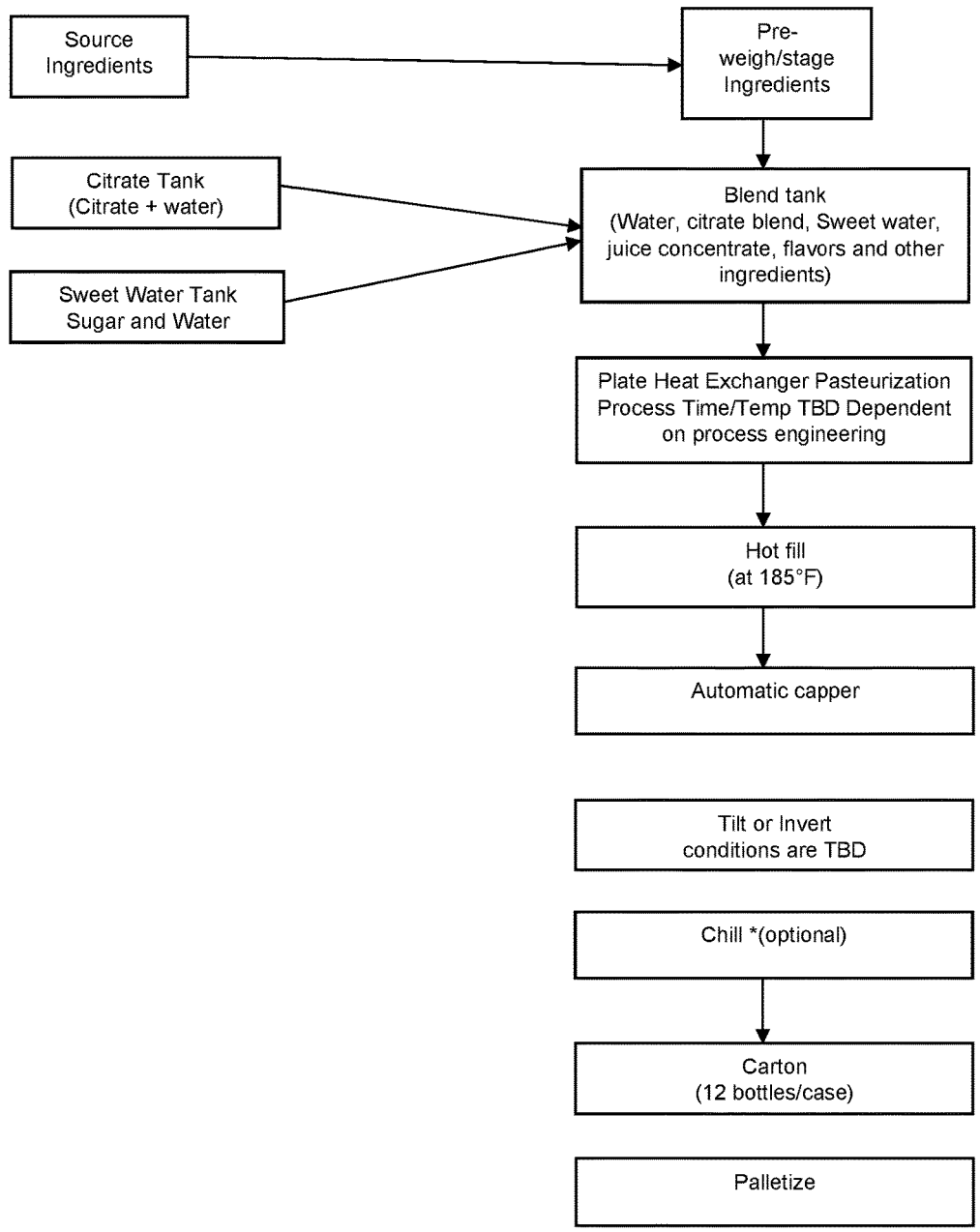

FIGS. 1 and 2 are schematic representations of methods (processes) by which citrate-rich beverages can be produced.

In the method, components (one or more citrate-containing juice(s) (e.g., citrate-containing juice(s) in ready-to-drink/not concentrated form and/or citrate-containing juice concentrate(s)) and, in some embodiments, one or more additional source(s) of citrate which is not a citrate-containing juice) are combined, using known methods, in sufficient amounts to produce a citrate-rich beverage in which the citrate content is as described in detail above.

In one embodiment, the method comprises: (a) hydrating a citrate blend, by combining source(s) of citrate (e.g., non-juice sources of citrate) with water and producing a hydrated citrate blend (which includes the citrate source(s) in water); (b) optionally, adding or combining the hydrated citrate blend with sugar and/or sugar alternative, if desired (an optional addition/combination) and mixing the resulting combination as needed to dissolve the sugar and/or sugar alternative in the hydrated citrate blend; (c) combining the product of (a), if no sugar or sugar alternative is used or the product of (b), if sugar and/or sugar alternative is used, with juice concentrate(s) (concentrate(s) of the citrate-containing juices to be included in the citrate-rich beverage), flavoring(s) and additional components and blending/mixing the resulting combination to dissolve the components, thereby producing a blended product; (d) processing the blended product under conditions under which the blended product is pasteurized, thereby producing a pasteurized blended product which is a citrate-rich beverage. The method further comprises processing the citrate-rich beverage to produce a packaged citrate-rich beverage. In one embodiment, the citrate blend of (a) comprises zinc citrate, magnesium citrate and monosodium citrate anhydrous. It is combined with sufficient water to hydrate the citrate blend (e.g., combined with 100° F. water) and the combination is mixed, producing the citrate blend in water, referred to as a hydrated citrate blend. If sugar and/or a sugar alternative is included, it is combined with the hydrated citrate blend and the resulting combination is mixed until the sugar is dissolved. In some embodiments (e.g., when the quantity/volume of components is small), the resulting combination is mixed for about 1 minute. The resulting product is combined with juice concentrate(s) (concentrate(s) of the citrate-containing juices to be included in the citrate-rich beverage), flavoring(s) and additional components and the resulting combination is mixed or blended, thereby producing a blended product. The blended product is treated under conditions that result in its pasteurization, thereby producing a pasteurized blended product that is a pasteurized citrate-rich beverage. For example, the blended product is pasteurized under process conditions such as bringing the product up to a temperature of about 185° F. (e.g., for about 3 seconds, using a flow rate of about 13.5 ml/minute).

The pasteurized citrate-rich beverage is further processed, using known methods, to prepare it for storage and sale. For example, the citrate-rich beverage can be hot filled (e.g., at about 185° F.) into containers (e.g., glass, plastic, juice box, carton, retort pouch, can), which are then further processed, as needed, to prepare them for storage and sale. For example, the containers are closed (capped, sealed), inverted briefly, chilled (e.g., in an ice bath for about 10 minutes or more) and the final product is placed in cartons. In addition to a hot-filled process, aseptic packaging can be used.

In one embodiment, the method comprises combining two citrate-containing juices, such as lemon juice concentrate and cranberry juice concentrate; water, sugar and non-juicecitrate sources (citrate blend), such as zinc citrate, potassium citrate, magnesium citrate (anhydrous) and monosodium citrate, under conditions that result in production of a citrate-rich beverage in which the citrate level is about 5600 mg/8 ounce serving. In a further embodiment, the method comprises combining a citrate-containing juice, such as orange juice concentrate; sugar; and non-juice citrate sources (citrate blend), such as citric acid, zinc citrate and potassium citrate; and flavoring, such as fruit flavor (e.g., strawberry flavor and orange flavor), under conditions that result in production of a citrate-rich beverage in which the citrate level is about 5500 mg/8 ounce serving. In another embodiment, the method comprises combining two citrate-containing juices, such as lemon juice concentrate and cherry juice concentrate; sugar; non-juice citrate sources (citrate blend), such as zinc citrate, potassium citrate, magnesium citrate (anhydrous) and monosodium citrate; and flavoring, such as raspberry flavor, under conditions that result in production of a citrate-rich beverage which contains about 5300 mg citrate/8 ounce serving.

In another embodiment, the method comprises combining two or more citrate-containing juices, such as lemon juice concentrate and cranberry juice concentrate; water: sugar and non-juice citrate sources (citrate blend), such as zinc citrate, potassium citrate, magnesium citrate (anhydrous) and monosodium citrate, under conditions that result in production of a citrate-rich beverage in which the citrate level is from about 2000 mg to about 6400 mg/8 ounce serving.

In alternative embodiments, two or more of the following citrate-containing juices, typically in the form of juice concentrates, are combined, orange juice, lemon juice, lemonade, tangerine juice, pineapple juice, grape juice, cranberry juice and grapefruit juice; sufficient water is combined with the juice concentrate(s). The two or more citrate-containing juices (e.g., in the form of juice concentrates) are combined in varying concentrations that result in a citrate-rich beverage that comprises from about 2500 mg to about 6400 mg per 8 ounce serving, such as about 4500-5500 mg per 8 ounce serving. For example, lemon juice, lime juice, orange juice, grapefruit juice or any combination of two, three or four of lemon juice, lime juice, orange juice and grapefruit juice can be combined in appropriate quantities to produce a citrate-rich beverage.

In a further embodiment, a citrate-rich beverage comprises two or more of the following citrate-containing juices: orange juice, lemon juice, tangerine juice, pineapple juice, grape juice, cranberry juice and grapefruit juice and an additional source of citrate that is not a citrate-containing juice (non-juice citrate source), such as a source of one or more of the following: potassium citrate, sodium citrate, calcium citrate, zinc citrate, magnesium citrate, citric acid. They are combined in sufficient amounts to produce a citrate-rich beverage in which the citrate content is from about 2500 mg to about 6400 mg per 8 ounce serving, such as about at least 4500 mg per 8 ounce serving. The amount of each type of citrate source (citrate-containing juice, other source of citrate that is not a citrate-containing juice) needed to produce acitrate-rich beverage in which the citrate content is the desired amount (e.g., from about 2000 mg to about 6400 mg per 8 ounce serving, such as about 4500 mg per 8 ounce serving) can be determined empirically, if the citrate content of each component is known or is determined, if necessary, using known methods. For example, the citrate content of juices, such as orange juice, lemon juice, and grapefruit juice is shown in Table 1 and of additional juices in Table 5. The citrate-rich beverages described herein, which contain blends of natural juices, such as, but not limited to, citrus juices, increase urinary citrate excretion and hydration and will offer consumers at risk for stone formation an adjunct to medical therapy. Described herein, in addition to a ready-to-drink beverage, are concentrates in a solid (powder mix) or a liquid form for reconstitution into a citrate-rich beverage. There are many possible combinations of components described herein that can be used to produce citrate-rich beverages, as well as to produce the powder and liquid concentrates that can be used to produce citrate-rich beverages. The liquid formulations, both ready to use and concentrated, may be sterilized by such methods as heat treatment, to inhibit contamination and increase shelf-life.

TABLE 1

Citric Acid Content of Various Fruit Juices and Commercially-Available Juice Formulations (Grams per Liter)*

| Product | Type of product | n | Total citric acid Mean | SD |
|---|---|---|---|---|
| Lemon juice | fresh, from fruit | 2 | 48.0 | 3.82 |
| Lime juice | fresh, from fruit | 2 | 45.8 | 6.86 |
| Lemon juice, Concord Foods | juice concentrate | 1 | 39.2 | |
| Lime juice, ReaLime 100% | juice concentrate | 1 | 35.4 | |
| Lemon juice, ReaLemon 100% | juice concentrate | 1 | 34.1 | |
| Grapefruit juice, Florida's Ruby Red | ready-to-consume | 1 | 25.0 | |
| Orange juice, Tropicana Pure Premium | ready-to-consume | 1 | 16.9 | |
| Orange juice, Tropicana Light 'n Healthy | ready-to-consume | 1 | 16.7 | |
| Orange juice | fresh, from fruit | 2 | 9.10 | 1.98 |
| Limeade/limonada, Minute Maid | ready-to-consume | 1 | 7.30 | |
| Lemonade, Newman's Own | ready-to-consume | 1 | 6.70 | |
| Lemonade, Florida's Natural | ready-to-consume | 1 | 6.20 | |
| Lemonade, Minute Maid Light | ready-to-consume | 1 | 5.20 | |
| Raspberry lemonade, Minute Maid | ready-to-consume | 1 | 5.00 | |
| Lemonade, Tropicana | ready-to-consume | 4 | 4.83 | 0.61 |
| Pink lemonade, Minute Maid | ready-to-consume | 1 | 4.80 | |
| Lemonade, Tropicana Sugar-Free | ready-to-consume | 3 | 4.60 | 0.44 |
| Lemonade, Minute Maid | ready-to-consume | 1 | 4.40 | |
| Lemonade mix, Crystal Light | drink mix | 2 | 4.20 | 0.71 |
| Pink lemonade mix, Crystal Light | drink mix | 2 | 3.40 | |
| Raspberry lemonade mix, Crystal Light | drink mix | 1 | 3.10 | |
| Lemonade mix, Kool-Aid Sugarfree | drink mix | 1 | 2.10 | |
| Lemonade mix, Country Time | drink mix | 1 | 1.60 | |
| Crystallized lemon, True Lemon | dry mix | 1 | 0.92 | |

*Penniston, K. L. et al., J Endourol. 2008 March; 22(3): 567-570. Quantitative Assessment of Citric Acid in Lemon Juice, Lime Juice, and Commercially-Available Fruit Juice Products

TABLE 2

Components of commercially-available products

| | Citrate g/l | Citrate mg/ 8 oz | Carbs g/ 8 oz | Calories/ 8 oz |
|---|---|---|---|---|
| Lemon Juice | 48 | 9896 | 19.6 | 57 |
| Tropicana Orange Juice | 16.7 | 3443 | 26 | 110 |
| Lemonade Minute Maid Light | 5.2 | 1072 | 4 | 5 |
| Lemonade Minute Maid | 4.4 | 907 | 28 | 100 |
| Raspberry Lemonade Minute Maid | 5.0 | 1030 | 29 | 110 |
| Cranberry Lemonade Minute Maid | | | 32 | 120 |

TABLE 3

Citrate-rich beverages

| Name | Citrate g/l | Citrate mg/8 oz | Carbs g/8 oz | Calories |
|---|---|---|---|---|
| 1 | 23.8 | 5640 | 33 | 130 |
| 2 | 22.6 | 5350 | 33 | 130 |
| 3 | 23.3 | 5510 | 28 | 110 |

TABLE 4

Examples of sources of citrate

| Ingredient Name | Supplier |
|---|---|
| Zinc Citrate | Jungbunzlauer |
| Tri magnesium Citrate Anhydrous | Jungbunzlauer |
| Potassium Citrate | Jungbunzlauer |
| Monosodium Citrate | Jungbunzlauer |
| Citric Acid | Jungbunzlauer |
| Lemon Juice Concentrate | VitaPakt |
| Orange Juice Concentrate | VitaPakt |
| Cranberry Juice Concentrate, Essence Returned | Ocean Spray |

TABLE 5

| | SODIUM (mEq/liter) | POTASSIUM (mEq/liter) | CALCIUM (mg/liter) | MAGNESIUM (mg/liter) | CITRATE (mg/liter) | OXALATE (mg/liter) |
|---|---|---|---|---|---|---|
| Apple | 1.6 | 28.4 | 41 | 43 | 52.1 | 12.1 |
| Orange | 0.5 | 53.3 | 96 | 110 | 8,140 | Too low to detect |
| Grape | 0.2 | 8.3 | 34 | 44 | 1,735 | Too low to detect |
| Tangerine | 0.5 | 40.2 | 54 | 97 | 8,523 | 5.5 |

TABLE 5-continued

| | SODIUM (mEq/liter) | POTASSIUM (mEq/liter) | CALCIUM (mg/liter) | MAGNESIUM (mg/liter) | CITRATE (mg/liter) | OXALATE (mg/liter) |
|---|---|---|---|---|---|---|
| Pineapple | None Detected | 30.4 | 105 | 116 | 5,860 | 20.5 |
| Limeade | 0.9 | 4.2 | 34 | 13 | 6,648 | Too low to detect |
| Lemonade | 0.1 | 0.5 | 11 | 10 | 6,189 | Too low to detect |
| Pineapple-orange-banana | 0.2 | 44 | 88 | 118 | 6,285 | 14.8 |
| Grapefruit | 0.1 | 37.7 | 101 | 96 | 14,500 | 8.1 |

Resnick, MI, Pak, CYC. UROLITHIASIS A MEDICAL AND SURGICAL REFERENCE. W. B. Saunders Company, 1990. p. 162.

Example 1 Citrate Blend Formulations

Flavor profiles were identified that can act as vehicle to deliver high citrate level beverage that cater to consumer flavor interest. Marketable flavor profiles against prominent citrate sources were identified. Formulations prototype development include lemonade, orange and/or pineapple.

Bench top experiments were conducted to assess the optimal level of citrate that could make a health impact while maintaining a quality flavor profile and an appropriated caloric level. Samples were developed and prototypes presented included: Cranberry Lemonade, Berry Lemonade, Orange Cranberry, Orange Pineapple and Orange-Pineapple-Mango.

Values in the left columns were lab reported (citrate, Mg, Zn, K and Na) results. Values in the right columns were calculated values (citrate, Mg, Zn, K and Na). Actual analytical were conducted at Covance Laboratories.

The target for magnesium was 350 mg/serving. However, the daily value (DV) for Mg is 400 mg/serving. Some prototypes were formulated slightly above the 350 mg/serving target to minimize the use of potassium and sodium.

Calculated values were based on 8 fluid ounces (236.6 g). Analytical results are reported slightly higher as the values account for specific gravity (density) value at ~1.065 g/mL.

Minimum citrate, magnesium, potassium, zinc and sodium values were calculated by accounting for the nutrients present in the formula without the addition of the citrate blends (i.e. magnesium citrate, potassium citrate, zinc citrate and/or sodium citrate). Calculations were prepared using the reported values in the raw material specifications.

Example 2 Method of Manufacture

Samples were batch prepared and then pasteurized. The order of addition was as follows:
1. Blend citrates+water, heat to at least 100° F., mix until dissolved.
2. Add sugar, mix until dissolved.
3. Add concentrates and flavor, mix until dissolved.
4. Heat treat to 185° F. (pasteurize)
5. Hot fill in glass bottles (at 185° F.)
6. Invert Prototype processing assessment samples were prepared using a pilot scaled plate heat exchanger (Armfield FT43A). In order to process a shelf stable, hot-fill process, product was processed above the minimal food safety recommendations (FDA Juice Guidance recommends heat processing at juice at 160° F. for 3 seconds). Conservative hot fill processing conditions were used for pilot plant prototypes using a 185° F. (for at least 3 seconds) and a flow rate of 13.5 ml/min. This process condition could likely be reduced once a final process operation is considered. Hot filling at 185° F. (with inversion) was done to ensure that spoilage organisms were not introduced during filling. FDA guidance for food safety juice processing was used as a reference for juice time/temperature conditions

What is claimed is:

1. A method of fortifying a natural juice for the prevention of urolithiasis producing a fortified natural juice consisting of the steps of:
    selecting two a citrate-containing juices selected from the group consisting of orange juice, lemon juice, lime juice, tangerine juice, pineapple juice, grape juice, cranberry juice, and grapefruit juice, said citrate-containing juice containing only naturally occurring plant protein;
    adding an additional non-juice citrate blend, said citrate blend consisting of zinc citrate, and at least one citrate selected from the group consisting of potassium citrate, magnesium citrate anhydrous, and monosodium citrate, wherein said citrate blend is added in sufficient amounts to produce a citrate-rich beverage in which the citrate content is from 4500 mg to 6400 mg per 8 ounce serving, wherein said citrate-rich beverage contains no added protein; and
    adding at least one nutrient selected from the group consisting of soluble calcium, other mineral supplements and vitamin supplements, soluble fiber; and
    adding water and a sweetener, wherein said sweetener is selected from the group consisting of sucrose, fructose, glucose, galactose, maltose, lactose, honey, stevia, erythritol, xylitol, sorbitol, and combinations thereof.

2. A method of fortifying a natural juice for the prevention of urolithiasis producing a fortified natural juice consisting of the steps of:
    selecting a citrate-containing juice selected from the group consisting of orange juice, lemon juice, lime juice, tangerine juice, pineapple juice, grape juice, cranberry juice, and grapefruit juice, said citrate-containing juice containing only naturally occurring plant protein;
    adding an additional non-juice citrate blend, said citrate blend consisting of zinc citrate, and at least one citrate selected from the group consisting of potassium citrate, magnesium citrate anhydrous, and monosodium citrate, wherein said citrate blend is added in sufficient amounts to produce a citrate-rich beverage in which the citrate content is from 4500 mg to 6400 mg per 8 ounce serving, wherein said citrate-rich beverage contains no added protein; and
    adding at least one nutrient selected from the group consisting of soluble calcium, other mineral supplements and vitamin supplements, soluble fiber; and adding a flavoring, optionally wherein the flavoring is a non-citrate containing juice, and a sweetener, wherein said sweetener is selected from the group consisting of sucrose, fructose, glucose, galactose, maltose, lactose, honey, stevia, erythritol, xylitol, sorbitol, and combinations thereof.

3. A method of fortifying a natural juice for the prevention of urolithiasis producing a fortified natural juice consisting of the steps of:
  selecting two a citrate-containing juices selected from the group consisting of orange juice, lemon juice, lime juice, tangerine juice, pineapple juice, grape juice, cranberry juice, and grapefruit juice, said citrate-containing juice containing only naturally occurring plant protein;
adding an additional non-juice citrate blend, said citrate blend consisting of zinc citrate, and at least one citrate selected from the group consisting of potassium citrate, magnesium citrate anhydrous, and monosodium citrate, wherein said citrate blend is added in sufficient amounts to produce a citrate-rich beverage in which the citrate content is from 4500 mg to 6400 mg per 8 ounce serving, wherein said citrate-rich beverage contains no added protein; and
adding at least one nutrient selected from the group consisting of soluble calcium, other mineral supplements and vitamin supplements, soluble fiber; and
adding a sweetener, wherein said sweetener is selected from the group consisting of sucrose, fructose, glucose, galactose, maltose, lactose, honey, stevia, erythritol, xylitol, sorbitol, and combinations thereof, and adding a flavoring, optionally wherein the flavoring is a non-citrate containing juice.

* * * * *